United States Patent
Matsumoto

(10) Patent No.: US 6,692,125 B2
(45) Date of Patent: Feb. 17, 2004

(54) OPHTHALMOLOGIC APPARATUS

(75) Inventor: Kazuhiro Matsumoto, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 82 days.

(21) Appl. No.: 09/969,771

(22) Filed: Oct. 4, 2001

(65) Prior Publication Data

US 2002/0044257 A1 Apr. 18, 2002

(30) Foreign Application Priority Data

Oct. 18, 2000 (JP) .......................................... 2000-317701

(51) Int. Cl.[7] .................................................. A61B 3/14
(52) U.S. Cl. ...................................................... 351/206
(58) Field of Search ................................. 351/200, 205, 351/206, 207, 221, 216, 246, 210; 600/318

(56) References Cited

U.S. PATENT DOCUMENTS

| | | | |
|---|---|---|---|
| 5,886,768 A | * 3/1999 | Knopp et al. | ................ 351/212 |
| 5,905,563 A | * 5/1999 | Yamamoto | ................ 351/210 |
| 6,295,172 B1 | 9/2001 | Yamamichi et al. | |
| 6,477,394 B2 | * 11/2002 | Rice et al. | ................ 600/318 |

* cited by examiner

Primary Examiner—George Manuel
(74) Attorney, Agent, or Firm—Fitzpatrick, Cella, Harper & Scinto

(57) ABSTRACT

An ophthalmologic apparatus for observations and photographs of an eye includes a body; an optical system including an image pickup device integrated in the body for picking up an image of an eye; a mount provided on the body for mounting auxiliary units thereon; an optical selector for selecting whether the image of the eye is to be guided to the image pickup device or to the auxiliary unit mounted on the mount; and a controller for deciding whether the image of the eye is to be guided to the image pickup device or to the auxiliary unit according to the kind of the auxiliary unit mounted on the mount and controlling the optical selector for observation and for photographing independently.

17 Claims, 7 Drawing Sheets

FIG. 7
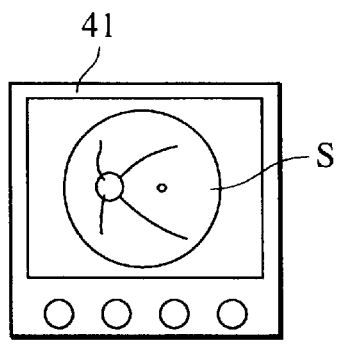
FIG. 8
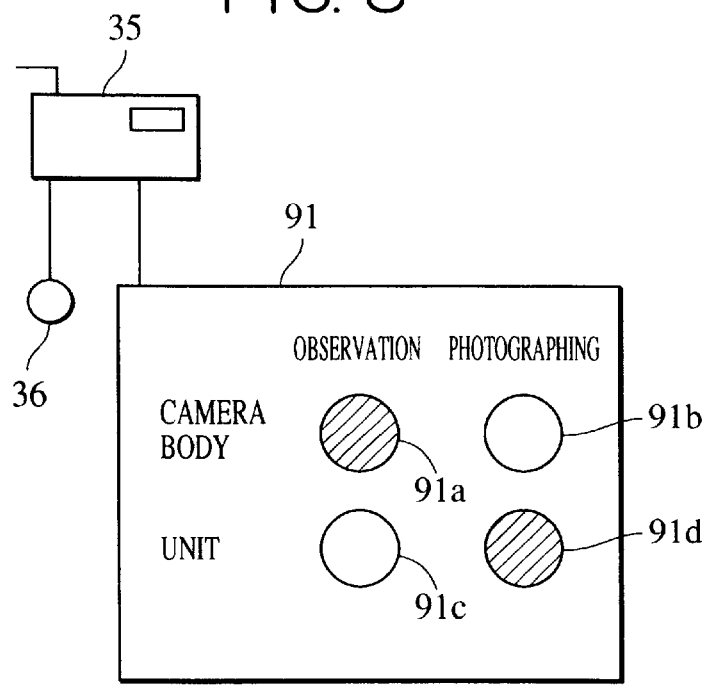
FIG. 9
APPARATUS SPECIFIED BY SWITCH DOES NOT AGREE WITH APPARATUS LOADED ON MOUNT

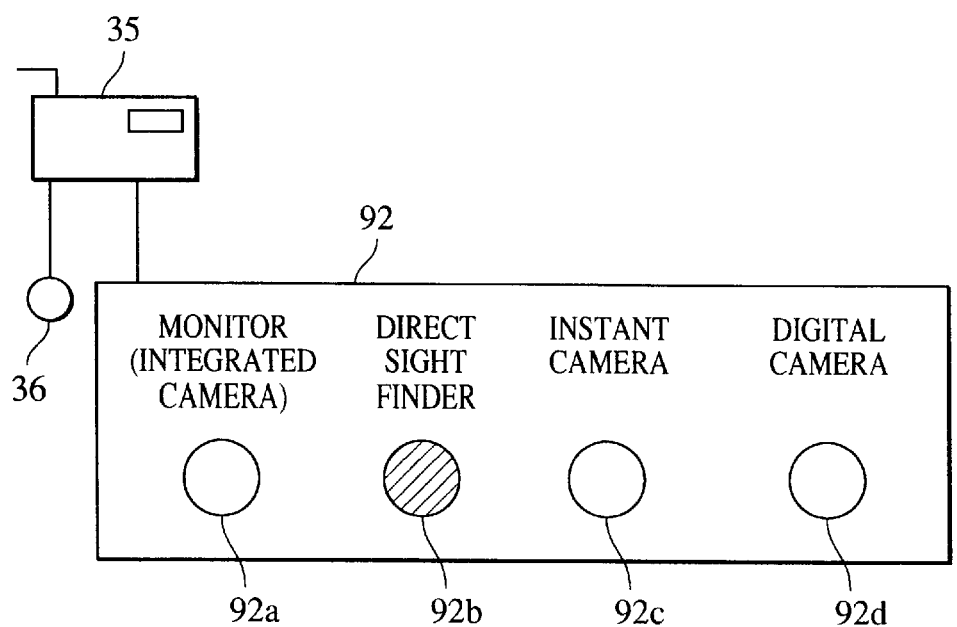

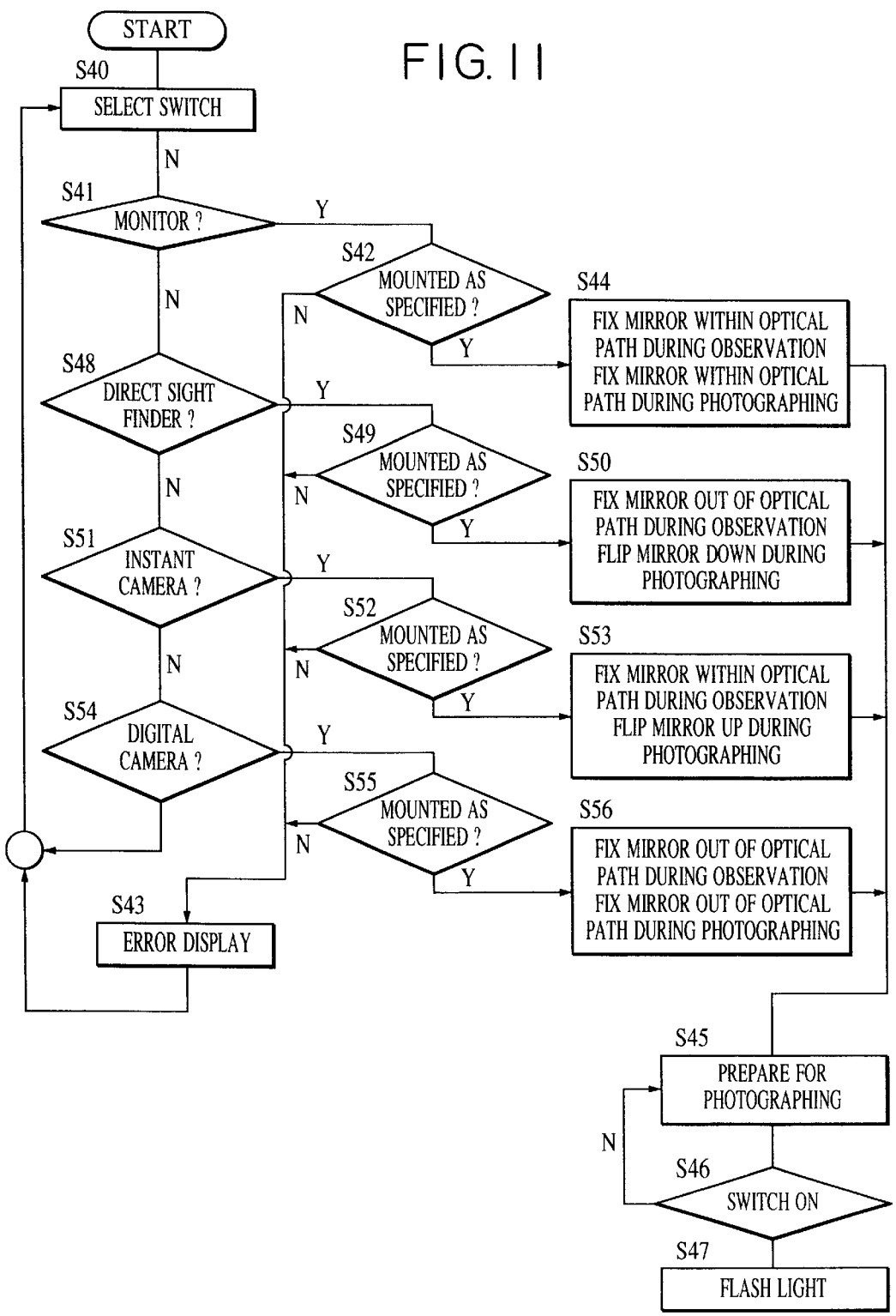

OPHTHALMOLOGIC APPARATUS

BACKGROUND OF THE INVENTION

1. Field of the Invention

The present invention relates to an ophthalmologic apparatus to be used in ophthalmic hospitals.

2. Description of the Related Art

The fundus camera as one of ophthalmologic apparatuses includes an optical system, for observing and/or photographing an eye fundus, integrated within the enclosure. There are enclosures that can accommodate auxiliary units having various functions via the respective mounts. The optical system for observations and photographs is generally constructed in such a manner that the optical path is diverged into an optical path for observing an eye fundus and an optical path for photographing the eye fundus by a flip-up mirror. The flip-up mirror is placed on the optical path when observing the eye fundus and the flip-up mirror is flipped up out of the optical path at the moment of photographing the eye fundus.

SUMMARY OF THE INVENTION

It is a major object of the present invention to improve the related art. One of the specific objects is to provide an ophthalmologic apparatus that can be used in various applications without increasing in complexity of the structure.

One of the embodiments of the present invention is an ophthalmologic apparatus for observing and photographing an eye, comprising:

a body;

an optical system including an image pickup device integrated in the body for picking up an image of an eye;

a mount provided on the body for mounting auxiliary units thereon;

an optical selector for selecting whether the image of the eye is to be guided to the image pickup device or to the auxiliary unit mounted on the mount; and a controller for deciding whether the image of the eye is to be guided to the image pickup device or to the auxiliary unit according to the kind of the auxiliary unit and controlling the optical selector for observation and for photographing independently.

Further objects, features and advantages of the present invention will become apparent from the following description of the preferred embodiments with reference to the attached drawings.

BRIEF DESCRIPTION OF THE DRAWINGS

FIG. 7 is an explanatory drawing of an image of an eye fundus;

FIG. 8 is a drawing of the switch panel;

FIG. 9 is an explanatory drawing of error messages displayed on the monitor display;

FIG. 10 is an explanatory drawing of another switch panel; and

FIG. 11 is a flow chart explaining a control procedure in the case where the switch panel is provided.

DESCRIPTION OF THE PREFERRED EMBODIMENTS

Figure 1:
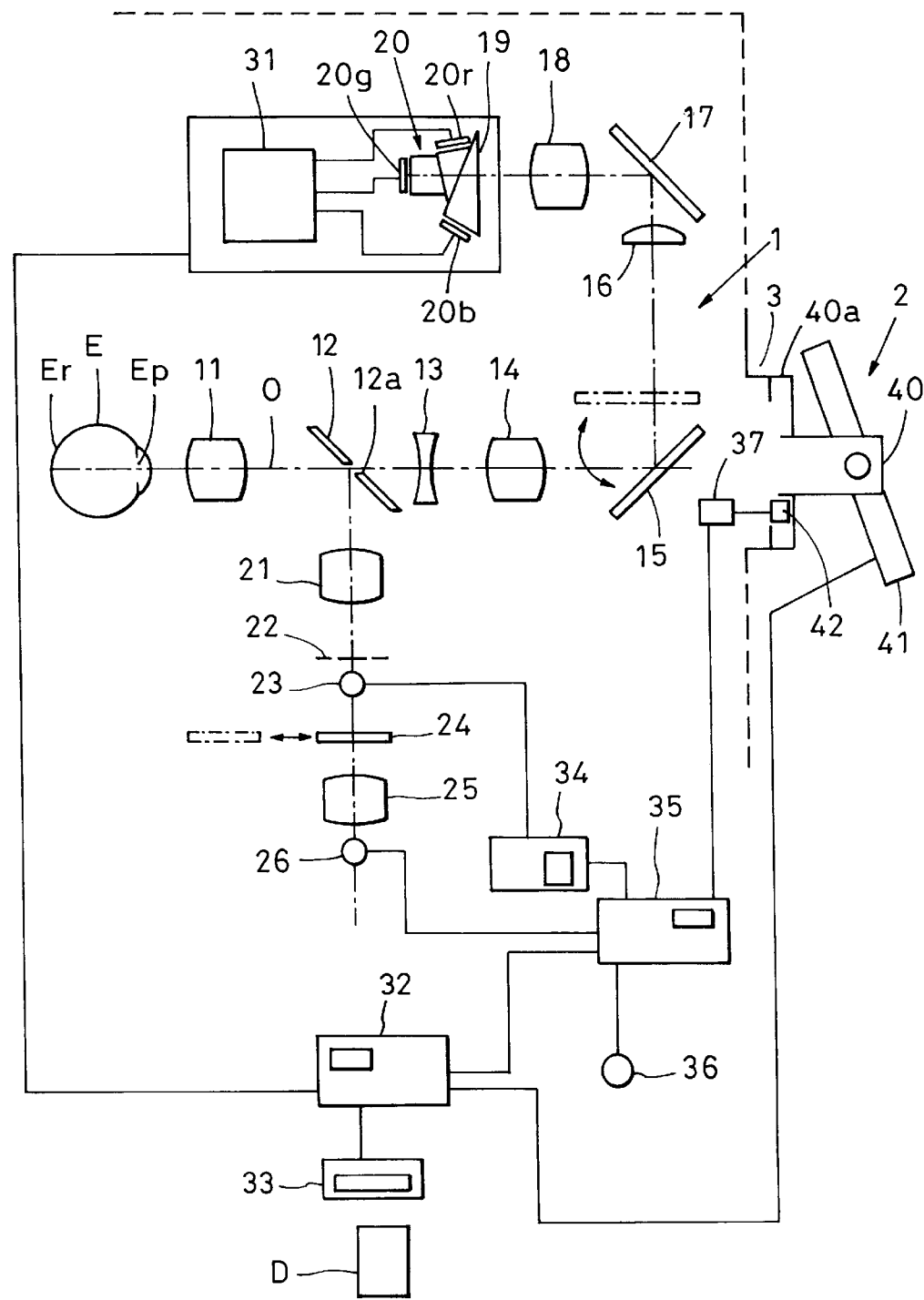
FIG. 1 is a block diagram of a fundus camera according to one embodiment.

FIG. 1 shows a block diagram of a fundus camera according to one embodiment of the present invention. The camera body 1 includes an optical system for observations and photographs for observing and photographing an eye E integrated therein. In a state shown in FIG. 1, the camera body 1 is mounted with a monitor display unit 2 for observing the patient's eye E on the rear panel thereof (on the side of the operator) via a mount 3. The camera body 1 can be provided with attached optional auxiliary units such as a direct sight finder unit, an instant film camera unit, and a digital camera unit described later instead of the monitor display unit 2 via a mount 3. The optical path O of the optical system for observations and photographs is aligned with the eye E by an operation device.

On the optical path O forward of the eye E, there are disposed an objective lens 11, a perforated mirror 12, a photographing aperture 12a, a focus lens 13 movable along the optical path, a taking lens 14, and a movable mirror 15 as an optical selector for diverging the optical path sequentially. In addition, a lens 16, a mirror 17, a lens 18, a color separation prism 19, and an image pickup device 20 are arranged in the direction of reflection of the mirror 15, so that an optical system for imaging an eye fundus as an integrated TV camera system is constructed. The color separation prism 19 has a function of separating a ray bundle into red light, green light, and blue light, and the image pickup device 20 comprises an element 20r for receiving the infrared ray and red light, an element 20g for receiving the green light, and an element 20b for receiving the blue light. In the direction where a light is incoming into the perforated mirror 12, there are arranged a relay lens 21, a ring aperture 22, a photographing light source 23 comprising a strobe tube, a wavelength selecting filter 24 detachably placed on the optical path for interrupting visible light and allowing an infrared ray to pass, a condensing lens 25, and an observation light source 26 comprising a halogen lamp or the like that emits fixed light including visible and infrared light, so as to construct a fundus illuminating optical system.

An image pickup device 20 is connected to an image control circuit 32 via a signal amplifier circuit 31, and the image control circuit 32 is in turn connected to a drive circuit 33 for writing/reading into/from the storage medium D. The photographing light source 23 is connected to the light emission control circuit 34 so that the light emission control circuit 34 controls the amount of light from the photographing light source 23. The observation light source 26, the image control circuit 32, and the light emission control circuit 34 are connected to a controller 35, and the controller 35 is provided with a photographing switch 36 and is connected with a contact point 37 disposed on the mount 3. The storage medium D may be MO, MD, DVD-RAM, VCR, or hard disk that can hold memory even without a supply of external electric power.

A monitor display unit 2 comprises a support 40 having a mount 40a to be attached on the mount 3 of the camera body 1, a liquid crystal monitor display 41 rotatably supported by the support 40, and a contact point 42 disposed within the mount 40a of the support 40. The contact point 42 of the monitor display unit 2 and the contact point 37 of the camera body 1 are automatically connected when the mount 40a of the monitor display unit 2 is connected to the mount 3 of the camera body 1. Therefore, the power is supplied from the controller 35 via the contact points 37, 42 to the monitor display unit 2, and the fact that the monitor display unit 2 is mounted on the camera body 1 is recognized, and the timing signal or the video data is received and transmitted with respect to the monitor display unit 2. The image control circuit 32 and the monitor display 41 are connected without the medium of the contact points 37, 42, so that the monitor display unit 2 can be separately installed.

Figure 2:
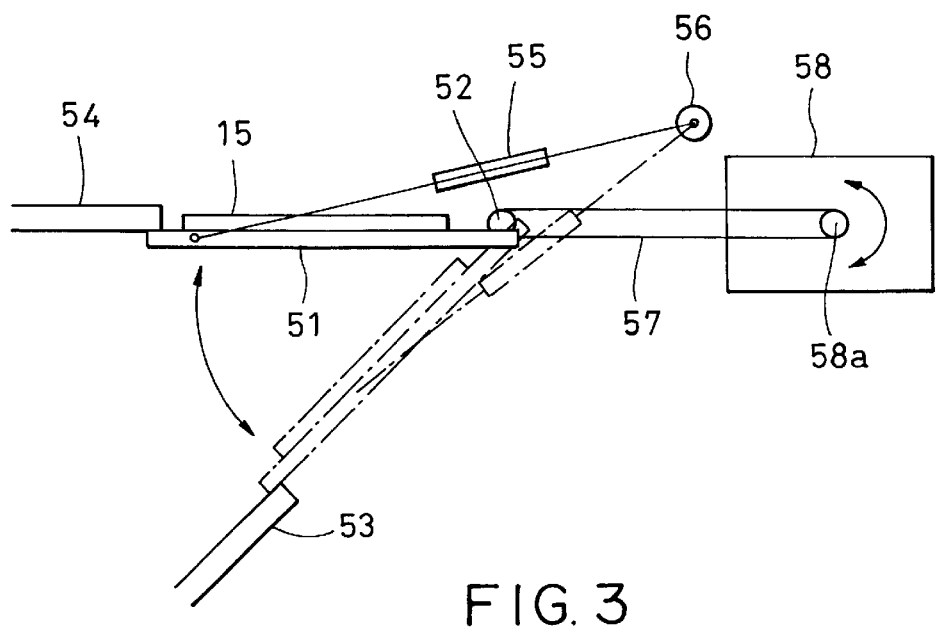
FIG. 2 is an explanatory drawing of the driving mechanism of the mirror.

As shown in FIG. 2, the mirror 15 is held by the holding plate 51 formed of a metal plate, and one end of the holding plate 51 is fixed to a revolving shaft 52. The holding plate 51 is driven to rotate integrally with the revolving shaft 52, and the range of rotation of the holding plate 51 is defined by the first limit member 53 and the second limit member 54. The holding plate 51 is connected via a helical extension spring 55 to the supporting portion 56 in the vicinity of the free end thereof, so that the holding plate 51 is urged toward the second limit member 54. The revolving shaft 52 is connected to an output shaft 58a of a motor 58 via a belt 57, and the motor 58 is in turn connected to the controller 35 described above.

When placing the mirror 15 in the optical path, the holding plate 51 is quickly rotated and moved into the optical path by the motor 58 and then brought into contact with the first limit member 53 to be prevented from further rotation, so that the mirror 15 is held on the optical path in a fixed manner. On the other hand, when removing the mirror 15 from the optical path, the holding plate 51 is flipped up out of the optical path very quickly by the reverse rotation of the output shaft 58a of the motor 58 and an urging force of the helical extension spring 55, and then brought into contact with the second limit member 54 so that further rotation thereof is prevented and the mirror 15 is held out of the optical path in a fixed manner.

Figure 3:
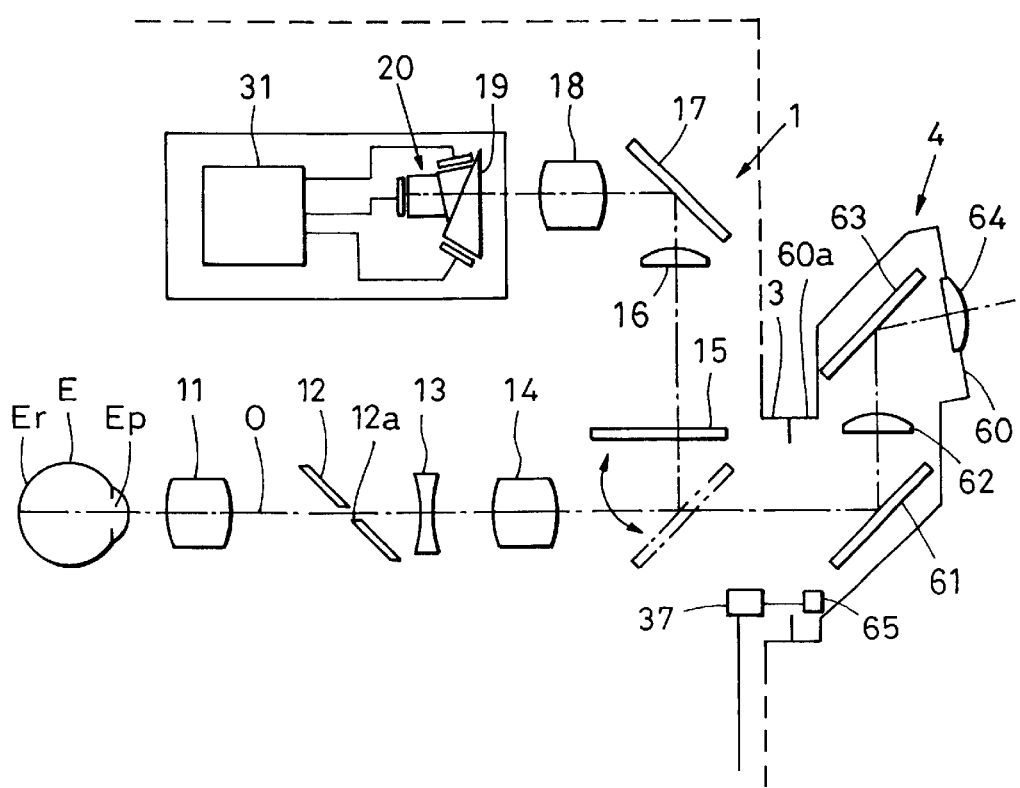
FIG. 3 is a drawing showing a state in which a direct sight finder unit is mounted.

FIG. 3 is a block diagram showing a state in which the direct sight finder unit 4 is mounted to the camera body 1 via the mount 3. The mount 60a of the enclosure 60 of the direct sight finder unit 4 is the same as the mount 40a of the monitor display unit 2. In the enclosure 60, there are disposed a mirror 61 reflecting a ray bundle from the taking lens 14, a lens 62 for imaging a ray bundle from the mirror 61, a mirror 63 for reflecting a ray bundle from the lens 62, and a finder lens 64 for allowing a ray bundle from the mirror 63 to pass through, so that a finder optical system is constructed. The mount 60a is provided with a contact point 65 to be connected to the contact point 37 of the camera body 1.

Figure 4:
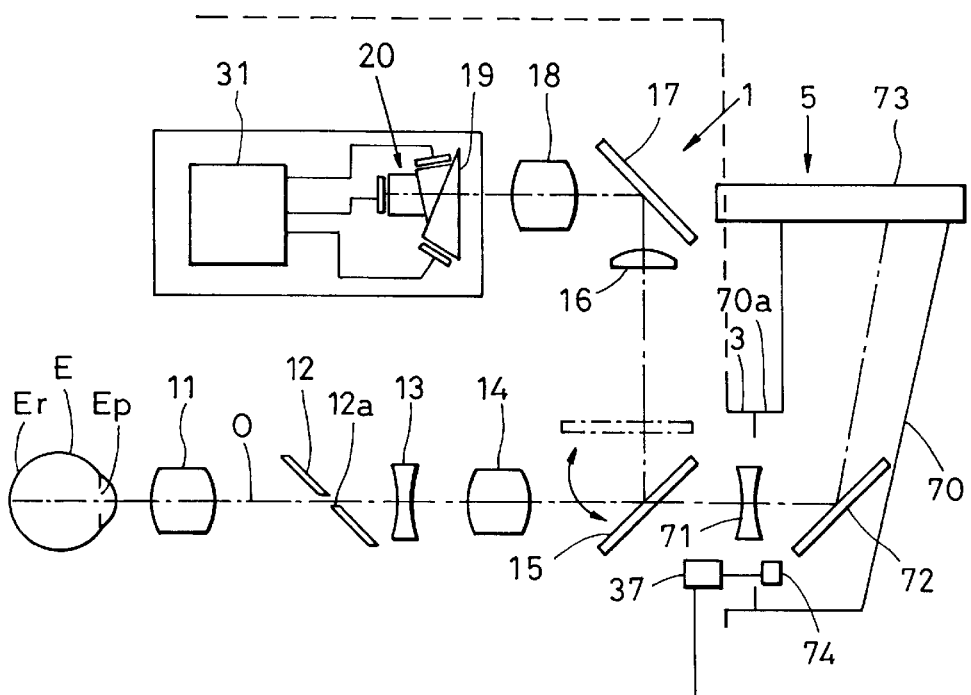
FIG. 4 is a drawing showing a state in which an instant film camera unit is mounted.

FIG. 4 is a block diagram showing a state in which an instant film camera unit 5 is mounted to the camera body 1 via the mount 3. The mount 70a of the enclosure 70 is also the same as the mount 40a of the monitor display unit 2. In the enclosure 70, there are disposed a lens 71 for allowing a ray bundle from the taking lens 14 to pass through, a mirror 72 for reflecting a ray bundle from the lens 71, and a film back 73 for receiving a ray bundle from the mirror 72, so that an imaging optical system is constructed. The mount 70a is provided with a contact point 74 to be connected to the contact point 37 of the camera body 1. The film back 73 accommodates instant film and a developing unit therein, and the instant film is disposed at a position conjugate to a pickup surface of the image pickup device 20.

Figure 5:
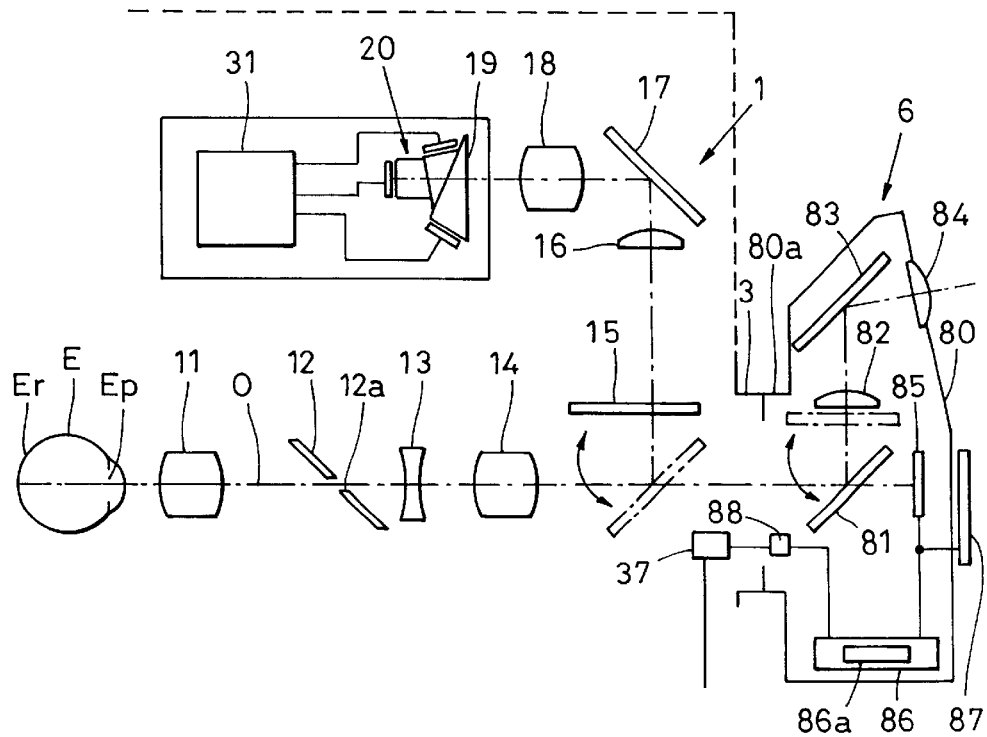
FIG. 5 is a drawing showing a state in which a digital camera unit is mounted.

FIG. 5 is a block diagram showing a state in which a digital camera unit 6 is mounted to the camera body 1 via the mount 3. The mount 80a of the enclosure 80 is also the same as the mount 40a of the monitor display unit 2. In the enclosure 80, there are disposed a flip-up mirror 81 for reflecting a ray bundle from the taking lens 14, a lens 82 having a focusing plate for imaging a ray bundle from the mirror 81, a mirror 83 for reflecting a ray bundle from the lens 82, and a finder lens 84 for allowing a ray bundle from the mirror 83 to pass through, so that a finder optical system is constructed. In the enclosure 80, there are also provided an image pickup device 85 for receiving a ray bundle from the taking lens 14, a drive circuit 86 having a memory 86a for storing signals from the image pickup device 85, and a liquid crystal monitor display 87 for displaying an image from the image pickup device 85. The mount 80a is provided with a contact point 88 to be connected to the contact point 37 of the camera body 1. The flip-up mirror 81 is constructed to evacuate out of the optical path at the moment of photographing, and the light receiving surface of the image pickup device 85 is disposed at a position conjugate to the pickup surface of the image pickup device 20 of the camera body 1.

Figure 6:
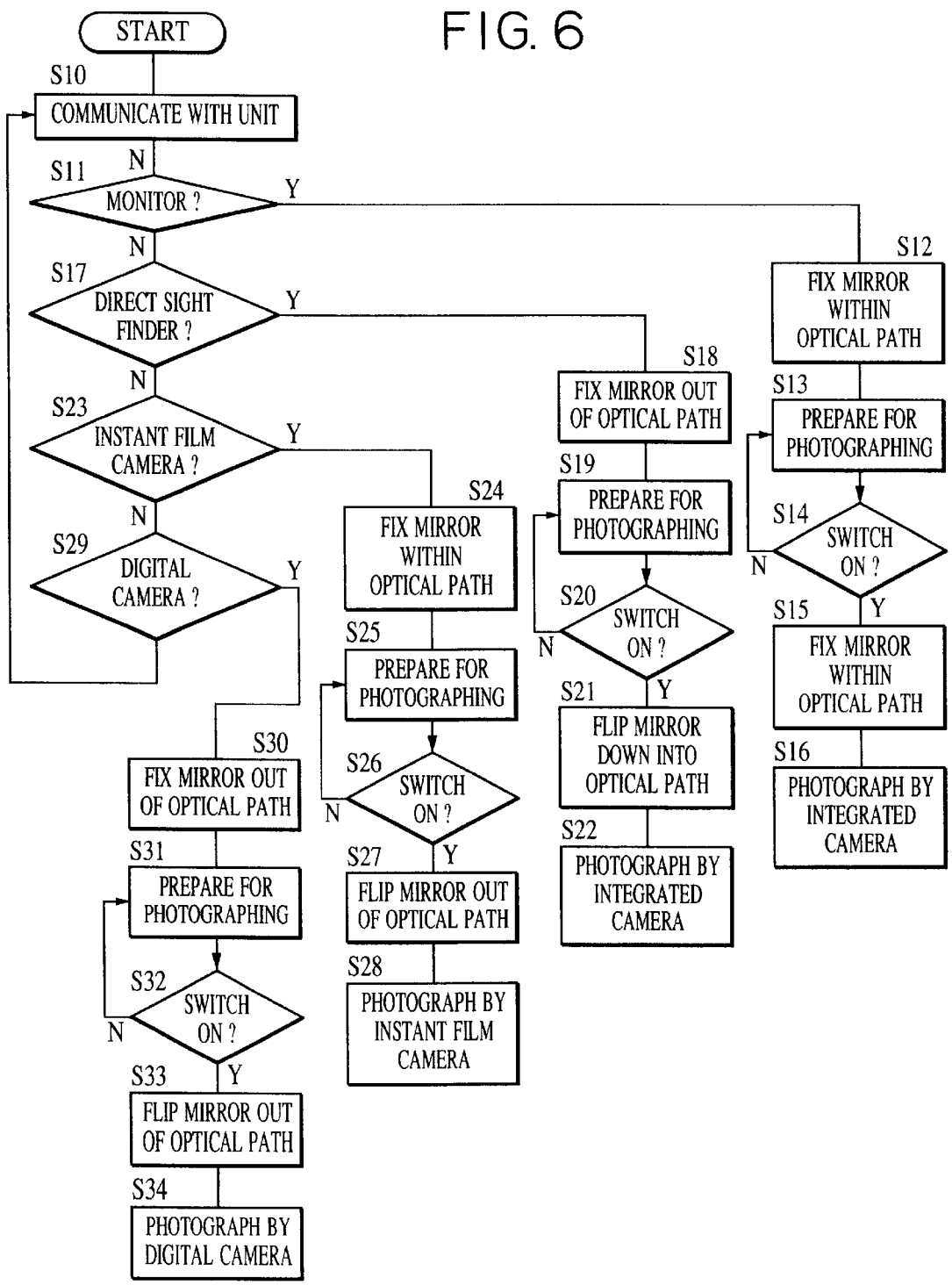
FIG. 6 is a flow chart explaining a control procedure thereof.

FIG. 6 is a flow chart describing the control procedure of the controller 35. In the step 10, it communicates with the unit 2, 4, 5 or 6 mounted thereon, and in the step 11, it determines whether or not the object mounted on the camera body 1 is the monitor display unit 2. When it is determined to be the monitor display unit 2, the procedure moves to the step 12, where the mirror 15 is fixed on the optical path, and in the step 13, registration, focusing, setting of the region, and the like are performed for preparation for photographing. In the step 14, it is determined whether or not the photographing switch 36 is ON. When the photographing switch 36 is ON, the procedure moves to the step 15, and when it is OFF, the procedure moves back to the step 13. In the step 15, the mirror 15 is maintained in the optical path in a fixed manner, and in the step 16, the image of an eye fundus is picked up by the image pickup device 20.

In the step 11, when the object is determined not to be the monitor display unit 2, the procedure moves to the step 17. In the step 17, it is determined whether or not the object mounted on the camera body 1 is the direct sight finder unit 4. When it is determined to be the direct sight finder unit 4, the procedure moves to the step 18. In the step 18, the mirror 15 evacuates out of the optical path, and in the step 19, preparation for photographing is carried out. Then, in the step 20, the state of the photographing switch 36 is determined as in the step 14. In the step 21, the mirror 15 is placed in the optical path, and in the step 22, the image of an eye fundus is picked up by the image pickup device 20.

When it is determined not to be the direct sight finder unit 4 in the step 17, the procedure moves to the step 23. In the step 23, it is determined whether or not the object mounted on the camera body 1 is the instant film camera unit 5. When it is determined to be the instant film camera unit 5, the procedure moves to the step 24. In the step 24, the mirror 15 is fixed in the optical path, and in the step 25, preparation for photographing is carried out. Then, in the step 26, the state of the photographing switch 36 is determined as in the step 14. In the step 27, the mirror 15 is flipped up, and in the step 28, the image of an eye fundus is photographed by the instant film in the film back 43.

In the step 23, when the object is determined not to be the instant film camera unit 5, the procedure moves to the step 29. In the step 29, it is determined whether or not the object mounted on the camera body 1 is the digital camera unit 6.

When it is determined to be the digital camera unit 6, the procedure moves to the step 30, and when it is determined not to be the digital camera unit 6, the procedure moves back to the step 10. In the step 30, the mirror 15 is fixed out of the optical path, and in the step 31, preparation for photographing is carried out. In the step 32, the state of the photographing switch 36 is determined as in the step 14. In the step 33, the flip-up mirror 81 is flipped out of the optical path, and in the step 34, the image of an eye fundus is picked up by the image pickup device 85.

In order to observe and photograph the eye fundus Er of an eye E, the test subject is seated in front of the fundus camera, and an infrared ray is irradiated on the eye fundus Er to observe the image of an eye fundus. Then, preparation for photographing such as registering, focusing, setting of the region, and the like is carried out, and then the eye fundus is photographed.

When the monitor display unit 2 is mounted on the camera body 1, signals from the contact point 42 are fed into the controller 35 via the contact point 37. The controller 35 identifies that it is the monitor display unit 2, places the mirror 15 and the wavelength selecting filter 24 in the optical path, and makes the observation light source 26 emit a light. The ray bundle from the observation light source 26 is converged on the condensing lens 25, and filtered through the wavelength selecting filter 24 to allow the infrared ray to pass through, so that the infrared ray goes through the photographing light source 23, the ring aperture 22, and the lens 21 onto the perforated mirror 12, and then irradiates though the objective lens 11 and a pupil Ep onto the eye fundus Er. The image of an eye fundus reflected off the eye fundus Er passes through the objective lens 11, the photographing aperture 12a of the perforated mirror 12, the focus lens 13, the taking lens 14, the mirror 15, the lens 16, the mirror 17, the lens 18, and the color separating prism 19 and is focused on the element 20r of the image pickup device 20. Electric signals from the element 20r are amplified at the signal amplifying circuit 31 with a prescribed gain and fed into the image control circuit 32, and then, as shown in FIG. 7, the image of the eye fundus S is displayed on the monitor display 41.

The operator observes the image of the eye fundus S displayed on the monitor display 41, registers by the use of the operation device, drives the focus lens 13 for focusing, and confirms the photographing region to complete preparation for photographing. Subsequently, when the photographing switch 36 is turned ON, the controller 35 makes the photographing light source 23 emit a light via the light emission control circuit 34. The ray bundle from the photographing light source 23 illuminates the eye fundus Er through the ring aperture 22, relay lens 21, the perforated mirror 12, the objective lens 11, and a pupil Ep. The image of the eye fundus is focused on all the elements 20r, 20g, and 20b of the image pickup device 20 through the objective lens 11, the photographing aperture 12a of the perforated mirror 12, the focus lens 13, the taking lens 14, the mirror 15, the lens 16, the mirror 17, the lens 18, and the color separating prism 19. Electrical signals from the elements 20r, 20g, and 20b are amplified at the signal amplifying circuit 31 at a prescribed gain, fed into the image control circuit 32, stored in the storage media D by the drive 33 as a still image and displayed on the monitor display 41.

When the direct sight finder unit 4 is mounted on the camera body 1, signals from the contact point 65 are fed into the controller 35 via the contact point 37. The controller 35 identifies that it is the direct sight finder unit 4, and makes the mirror 15 and the wavelength selecting filter 24 evacuate out of the optical path, and makes the observation light source 26 emit a light. The visible ray bundle emitted from the observation light source 26 illuminates the eye fundus Er through the condensing lens 25, the photographing light source 23, the ring aperture 22, the relay lens 21, the perforated mirror 12, the objective lens 11, and a pupil Ep. Then the image of the eye fundus enters into the direct sight finder unit 4 through the objective lens 11, the photographing aperture 12a of the perforated mirror 12, the focus lens 13, and the taking lens 14, and is focused in the vicinity of the lens 62 via the mirror 61. The operator looks into the finder lens 64, observes the image of the eye fundus focused in the vicinity of the lens 62 via the mirror 63 with the naked eye, and completes the preparation for photographing as in the case of the monitor display unit 2. Subsequently, when the photographing switch 36 is turned ON, the controller 35 places the mirror 15 on the optical path and make the photographing light source 23 emits a light. The ray bundle from the photographing light source 23 proceeds as described above, and the image of the eye fundus is stored in the recording medium D, and displayed on the separately installed monitor display 41. After the photographing is terminated, the controller 35 makes the mirror 15 evacuate out of the optical path.

Even when the features different from the integrated TV camera, for example, a TV camera for observation being capable of sensing infrared rays with high sensitivity, or the adaptor for mounting this TV camera for observation is mounted on the camera body 1 instead of mounting the direct sight finder unit 4, the same effect can be achieved.

When the instant film camera unit 5 is mounted on the camera body 1, signals from the contact point 74 are fed into the controller 35 via the contact point 37. The controller 35 identified that it is the instant film camera unit 5, places the mirror 15 and the wavelength selecting filter 24 on the optical path, and makes the observation light source 26 emit a light. The ray bundle from the observation light source 26 proceeds onto the eye fundus Er as an infrared ray as described above, and the image of the eye fundus is focused on the element 20r and displayed on the separately installed monitor display 41.

When the photographing switch 36 is turned ON after the preparation for photographing is completed, the controller 35 makes the mirror 15 evacuate out of the optical path and makes the photographing light source 23 emit a light. The ray bundle from the photographing light source 23 illuminates the eye fundus Er as described above, and the image of the eye fundus entered into the instant film camera unit 5 via the taking lens 14 is enlarged by the lens 71 and focused on the instant film in the film back 73 via the mirror 72. The controller 35 develops the instant film, feeds it out of the film back 73, and places the mirror 15 again on the optical path after photographing is terminated.

When the digital camera unit 6 is mounted on the camera body 1, signals from the contact point 88 are fed to the controller 35 via the contact point 37. The controller 35 identifies that it is the digital camera unit 6, places the mirror 15 and the wavelength selecting filter 24 out of the optical path, and makes the observation light source 26 emit a light. The ray bundle from the observation light source 26 proceeds as described above and illuminates the eye fundus Er by a visible light, and the image of the eye fundus passes through the taking lens 14 and is focused in the vicinity of the lens 82 through the flip-up mirror 81 in the digital camera unit 6. The operator looks into the finder lens 84 to observe the image of the eye fundus reflected off the mirror 83 with the naked eye, and completes preparation for photographing. Subsequently, when the photographing switch 36 is turned ON, the controller 35 flips the flip-up mirror 81 of the digital camera unit 6 out of the optical path, and makes the photographing light source 23 emit a light. The ray bundle from the photographing light source 23 illuminates the eye fundus Er as described above, and the image of the eye fundus passes through the taking lens 14 and is focused on the image pickup device 85. The controller 35 stores the image of the eye fundus picked up by the image pickup device 85 in the memory 86a of the drive circuit 86 and displays the same on the monitor display 87.

As described thus far, according to this embodiment, since the image of the eye fundus can be observed and photographed only by placing and removing the mirror 15 of the camera body 1 on/from the optical path, different kinds of units 2, 4–6 can be mounted on the camera body 1 without providing new optical path diverging mechanism, which results in improvement of convenience of photographing. In this case, by employing the same type of mounts 40a, 60a, 70a, and 80a for the respective units 2, 4–6, modification of the construction of the mount 3 of the camera body 1 is not necessary, and thus the construction is prevented from being increased in complexity. In addition, since the units 2, 4–6 mounted on the camera body 1 are identified by the controller 35, and the mirror 15 is automatically placed on or removed from the optical path based on the result of identification, failure of photographing can be prevented.

In the example described above, the unit 2, 4–6 mounted on the mount 3 of the camera body 1 is identified and the action of the mirror 15 is controlled based on the identification signals. However, as shown in FIG. 8, it is also applicable to provide a switch panel 91 having switches 91a–91d for selecting whether observation and photographing are to be made in the camera body 1 or in the units 2, 4–6, and to connect the switch panel 91 to the controller 35. In this case, when the shaded switches 91a, 91d are selected, as in the case where the instant film camera unit 5 is mounted on the camera body 1, the controller 35 places the mirror 15 on the optical path during observation, and makes it evacuate out of the optical path at the moment of photographing. In contrast to it, when other switches 91b, 91c are selected, as in the case where the direct sight finder unit 4 is mounted on the camera body 1, and the controller 35 makes the mirror 15 evacuate out of the optical path during observation and places it on the optical path at the moment of photographing. In the same manner, when the switches 91a, 91b are selected, as in the case where the monitor display unit 2 is mounted on the camera body 1, the controller 35 maintains the mirror 15 placed on the optical path. When the switches 91c, 91d are selected, as in the case where the digital camera unit 6 is mounted on the camera body 1, the controller 35 maintains the mirror 15 evacuated out of the optical path.

As is described thus far, by providing a switch panel 91, the image of the eye fundus can be observed by the monitor display 41 with the direct sight finder unit 4 mounted on the camera body 1, or photographed by the image pickup device 20 with the instant film camera unit 5 mounted on the camera body 1, which can significantly improve the usability of the apparatus. In this case, when the units 2, 4–6 do not satisfy the specified function selected by the switches 91a–91d of the switch panel 91 for observations and photographs, a user is notified by an error display as shown in FIG. 9.

In addition, instead of the switch panel 91 described above, it is also possible to provide a switch panel 92 having the switches 92a–92d that can select the units 2, 4–6 individually and connect the switch panel 92 to the controller 35 as shown in FIG. 10. In such a case, the controller 35 can be controlled according to the flow chart shown in FIG. 11. In the step 40, one of the switches 92a–92d is selected, and in the step 41, whether or not the object mounted on the camera body 1 is monitor display unit 2 is determined. When it is determined to be the monitor display unit 2, the procedure moves to the step 42. In the step 42, whether or not the monitor display unit 2 is mounted as specified is determined, and when it is not mounted as specified, the procedure moves to the step 43 while displaying an error message on the monitor display 41 as shown in FIG. 9. In contrast to it, when it is mounted as specified, the procedure moves to the step 44. In the step 44, the mirror 15 is fixed in the optical path at the time of observation and photographing, and then in the step 45, preparation for photographing is carried out. In the step 46, the state of the photographing switch 36 is determined, and in the step 47, the photographing light source 23 is made emit a light. Then, the steps 48–56 can be proceeded as the steps 41–47.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An ophthalmologic apparatus for observing and photographing an eye comprising:

a body;

an optical system including an image pickup device integrated in said body for picking up an image of an eye;

a mount provided on said body for mounting auxiliary units thereon;

an optical selector for selecting whether the image of the eye is to be guided to the image pickup device or to an auxiliary unit mounted on said mount during an observation operation and during a photographing operation; and a controller for deciding whether the image of the eye is to be guided to the image pickup device or to the auxiliary unit according to the kind of auxiliary unit mounted on said mount and controlling said optical selector for observation and for photographing independently.

2. An ophthalmologic apparatus according to claim 1, further comprising a switch connected to said controller for inputting the kind of auxiliary unit mounted on said mount.

3. An ophthalmologic apparatus according to claim 2, characterized in that the auxiliary unit includes at least one of a monitor display, a direct sight finder, an instant film camera, a digital camera, and an infrared ray observation camera.

4. An ophthalmologic apparatus according to claim 1, characterized in that said controller controls said optical selector to guide the image of the eye to said image pickup device both for observation and for photographing when the auxiliary unit mounted on said mount is a monitor display.

5. An ophthalmologic apparatus according to claim 1, characterized in that said controller controls said optical selector to guide the image of the eye to the auxiliary unit for observation, and to said image pickup device for subsequent photographing, when the auxiliary unit mounted on said mount is a direct sight finder.

6. An ophthalmologic apparatus according to claim 1, characterized in that said controller controls said optical selector to guide the image of the eye to said image pickup device for observation, and to the auxiliary unit for subsequent photographing, when the auxiliary unit mounted on said mount is an instant film camera.

7. An ophthalmologic apparatus according to claim 1, characterized in that said controller controls said optical selector to guide the image of the eye to the auxiliary unit both for observation and for subsequent photographing, when the auxiliary unit mounted on said mount is a digital camera.

8. An ophthalmologic apparatus according to claim 1, characterized in that said controller controls said optical selector to guide the image of the eye to the auxiliary unit for observation, and to said image pickup device for subsequent photographing, when the auxiliary unit mounted on said mount is an infrared ray observation camera.

9. An ophthalmologic apparatus for observing and photographing an eye comprising:
   a body;
   an optical system including an image pickup device integrated in said body for picking up an image of an eye;
   a mount provided on said body for mounting auxiliary units thereon;
   an optical selector for selecting whether the image of the eye is to be guided to said image pickup device or to an auxiliary unit mounted on said mount; and
   a controller,
   wherein said controller includes a first mode in which said optical selector is controlled to guide the image of the eye to said image pickup device for observation and to the auxiliary unit for photographing, and a second mode in which said optical selector is controlled to guide the image of the eye to the auxiliary unit for observation and to the image pickup device for photographing.

10. An ophthalmologic apparatus according to claim 9, characterized in that said controller further includes a third mode in which the image of the eye is guided to said image pickup device both for observation and for photographing, and a fourth mode in which the image of an eye is guided to the auxiliary unit both for observation and for photographing, and said controller selects any one of the modes.

11. An ophthalmologic apparatus according to claim 10, further comprising a switch connected to said controller for selecting whether observation and photographing are to be performed by said image pickup device or by the auxiliary unit.

12. An ophthalmologic apparatus according to claim 10, characterized in that said controller controls said optical selector according to the kind of the auxiliary unit mounted on said mount.

13. An ophthalmologic apparatus according to claim 12, characterized in that the auxiliary unit comprises at least one of a monitor display, a direct sight finder, an instant film camera, a digital camera, and an infrared ray observation camera.

14. An ophthalmologic apparatus for observing and photographing an eye, comprising:
   a body;
   an optical system including an image pickup device integrated in said body for picking up an image of an eye;
   a mount provided on said body for mounting auxiliary unit thereon;
   an optical selector for causing the image of the eye to be guided to either said image pickup device or to an auxiliary unit mounted on said mount during each of an observation operation and a photographing operation; and
   a controller controlling, in a first mode, said optical selector to guide the image of the eye to said image pickup device, and controlling, in a second mode, said optical selector to guide the image of the eye to the auxiliary unit, said controller independently selecting one of the first and second modes for each of the observation and photographing operations according to the type of auxiliary unit mounted on said mount.

15. An ophthalmologic apparatus according to claim 14, wherein said controller and the auxiliary unit each include an electrical contact, said electrical contacts are electrically connected when the auxiliary unit is mounted on said mount, said controller receives a signal from the auxiliary unit indicating the type of auxiliary unit mounted on said mounted when electrically connected thereto, and said controller selects one of the first and second modes during the observation operation and one of the first and second modes during the photographing operation according to the received signal.

16. An ophthalmologic apparatus according to claim 14, further comprising a switch panel for setting the controller to one of the first and second modes during the observation operation and one of the first and second modes during the photographing operation.

17. An ophthalmologic apparatus comprising:
   a body;
   an optical system for observing and photographing an eye;
   a mount provided on said body for mounting auxiliary units thereon;
   a controller for identifying the kind of auxiliary unit mounted on said mount and controlling the optical system of the apparatus based on the kind of auxiliary unit identified.

* * * * *

UNITED STATES PATENT AND TRADEMARK OFFICE
CERTIFICATE OF CORRECTION

PATENT NO.    : 6,692,125 B2
DATED         : February 17, 2004
INVENTOR(S)   : Kazuhiro Matsumoto It is certified that error appears in the above-identified patent and that said Letters Patent is hereby corrected as shown below:

<u>Column 6,</u>
Line 17, "make" should read -- makes --; and
Line 18, "emits" should read -- emit --.

<u>Column 8,</u>
Line 18, "made" should read -- made to --.

<u>Column 10,</u>
Line 34, "mounted" should read -- mount --; and
Line 50, "thereon;" should read -- thereon; and --.

Signed and Sealed this

Fifth Day of October, 2004

JON W. DUDAS
*Director of the United States Patent and Trademark Office*